(12) United States Patent
Shaw et al.

(10) Patent No.: US 10,489,649 B2
(45) Date of Patent: Nov. 26, 2019

(54) DRONE DATA LOCKER SYSTEM

(71) Applicant: AT&T Intellectual Property I, L.P., Atlanta, GA (US)

(72) Inventors: Venson Shaw, Kirkland, WA (US); Sangar Dowlatkhah, Alpharetta, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 121 days.

(21) Appl. No.: 15/718,754

(22) Filed: Sep. 28, 2017

(65) Prior Publication Data
US 2019/0095687 A1    Mar. 28, 2019

(51) Int. Cl.
*G06K 9/00* (2006.01)
*G06K 9/20* (2006.01)
(Continued)

(52) U.S. Cl.
CPC .......... *G06K 9/0063* (2013.01); *A61B 5/0022* (2013.01); *A61B 5/1171* (2016.02);
(Continued)

(58) Field of Classification Search
CPC ....... A61B 5/746; A61B 5/024; A61B 5/0022; A61B 5/0205; A61B 5/0002; A61B 5/0816; A61B 5/742; A61B 5/02055; A61B 5/021
(Continued)

(56) References Cited

U.S. PATENT DOCUMENTS

| 8,251,307 B2 | 8/2012 | Goossen |
| 8,909,391 B1 | 12/2014 | Peeters et al. |

(Continued)

FOREIGN PATENT DOCUMENTS

| CN | 104802986 A | 7/2015 |
| CN | 204846372 U | 12/2015 |

(Continued)

OTHER PUBLICATIONS

Gilbert, United States Department of Defense Research in Robotic Unmanned Systems for Combat Casualty Care, Defense Technical Information Center, dtic.mil, Aug. 13, 2010.

(Continued)

*Primary Examiner* — Mark S Blouin
(74) *Attorney, Agent, or Firm* — Haynes and Boone, LLP

(57) ABSTRACT

Systems for a drone data storage or data locker system include an unmanned aerial vehicle, or drone, which includes sensors, including an imaging sensor, a communications interface, and a memory storing identity data associated with one or more users and observation data associated with the one or more users which is collected on a continuous basis. The drone may navigate to an area including individuals, and obtain, using the sensors, sensor data corresponding to the individuals. The drone may determine, based on the obtained sensor data and the identity data, that one of the individuals corresponds to identity data of a user stored in the memory. The drone may determine that the user corresponding to the identity data requires medical assistance, using the sensors. The drone may transmit health data associated with the user corresponding to the identity data, which may be used to administer care to the user.

17 Claims, 9 Drawing Sheets

(51) Int. Cl.
  *A61B 5/00*     (2006.01)
  *A61B 5/1171*   (2016.01)
  *B64C 39/02*    (2006.01)
  *H04B 7/185*    (2006.01)
  *B64D 47/00*    (2006.01)
  *B60L 53/30*    (2019.01)

(52) U.S. Cl.
  CPC ............ *A61B 5/6887* (2013.01); *A61B 5/741* (2013.01); *A61B 5/747* (2013.01); *B64C 39/024* (2013.01); *G06K 9/00771* (2013.01); *G06K 9/00885* (2013.01); *G06K 9/209* (2013.01); *B60L 53/30* (2019.02); *B64C 2201/024* (2013.01); *B64C 2201/127* (2013.01); *B64C 2201/146* (2013.01); *B64D 47/00* (2013.01); *G06K 9/00362* (2013.01); *H04B 7/18506* (2013.01)

(58) Field of Classification Search
  USPC ....................................................... 340/573.1
  See application file for complete search history.

(56) References Cited

U.S. PATENT DOCUMENTS

| | | | |
|---|---|---|---|
| 8,948,935 B1 | 2/2015 | Peeters et al. | |
| 8,983,682 B1 | 3/2015 | Peeters et al. | |
| 9,307,383 B1 | 4/2016 | Patrick | |
| 9,422,139 B1* | 8/2016 | Bialkowski | B64C 39/024 |
| 9,434,473 B2 | 9/2016 | Peeters et al. | |
| 9,436,181 B2 | 9/2016 | Peeters et al. | |
| 9,580,173 B1 | 2/2017 | Burgess et al. | |
| 9,817,396 B1* | 11/2017 | Takayama | G05D 1/0038 |
| 2015/0148988 A1* | 5/2015 | Fleck | G05D 1/0011 |
| | | | 701/2 |
| 2015/0158587 A1* | 6/2015 | Patrick | B64C 39/024 |
| | | | 244/137.4 |
| 2015/0179038 A1 | 6/2015 | Daniel et al. | |
| 2016/0070260 A1 | 3/2016 | Levien et al. | |
| 2016/0096622 A1 | 4/2016 | Richardson | |
| 2016/0194069 A1 | 7/2016 | Taylor | |
| 2016/0221683 A1 | 8/2016 | Roberts et al. | |
| 2016/0244165 A1 | 8/2016 | Patrick et al. | |
| 2016/0311532 A1 | 10/2016 | Fleck | |
| 2017/0069214 A1 | 3/2017 | Dupray et al. | |
| 2017/0099076 A1 | 4/2017 | Feher | |
| 2017/0137124 A1 | 5/2017 | Walker et al. | |
| 2017/0334561 A1* | 11/2017 | Sopper | B64D 1/22 |
| 2018/0158551 A1* | 6/2018 | Bradley | G06K 9/00892 |

FOREIGN PATENT DOCUMENTS

| | | |
|---|---|---|
| CN | 204904034 U | 12/2015 |
| WO | WO 2016142967 A1 | 9/2016 |
| WO | WO 2016153223 A1 | 9/2016 |
| WO | WO 2016159481 A1 | 10/2016 |
| WO | WO 2017055985 A1 | 4/2017 |
| WO | WO 2017065347 A1 | 4/2017 |

OTHER PUBLICATIONS

Lum et al., Telesurgery Via Unmanned Aerial Vehicle (UAV) with a Field Deployable Surgical Robot, UCLA, UCLA EDU, Mar. 19, 2007.
Hotze, Robotic First Aid: Using a mobile robot to localise and visualise points of interest for first aid, Digitala Vetenskapliga Arkivet, diva-portal.org, Sep. 24, 2016.
Drone That Can Save Lives: Ambulance UAV Hints At Future Of Healthcare, RT, rt.com, Oct. 30, 2014.
Lippiello, Cartesian Impedance Control Of A UAV With A Robotic Arm, IFAC Proceedings vols. 45.22 (2012): 704-709.
Kim, Aerial Manipulation Using A Quadrotor With A Two Dof Robotic Arm, Intelligent Robots and Systems (IROS), 2013 IEEE/RSJ International Conference on. IEEE, 2013.
Arleo, Control Of Quadrotor Aerial Vehicles Equipped With A Robotic Arm, Control &Amp; Automation (MED), 2013 21st Mediterranean Conference on. IEEE, 2013.

* cited by examiner

DRONE DATA LOCKER SYSTEM

FIELD OF THE DISCLOSURE

This disclosure relates generally to drones, such as unmanned aerial vehicles, and, more particularly, to drone-based collection and storage of data related to users.

BACKGROUND

Drones, such as unmanned aerial vehicles (UAVs), are mobile platforms capable of acquiring (e.g., sensing) information, delivering goods, manipulating objects, etc., in many operating scenarios. Drones typically have the ability to travel to remote locations that are inaccessible to manned vehicles, locations that are dangerous to humans, or any other location. Upon reaching such locations, a suitably equipped drone may perform actions, such as acquiring sensor data (e.g., audio, images, video and/or other sensor data) at a target location, delivering goods (e.g., packages, medical supplies, food supplies, engineering materials, etc.) to the target location, manipulating objects (e.g., such as retrieving objects, operating equipment, repairing equipment etc.) at the target location, etc.

Drones are often controlled by a remote user from a command center (e.g., using a remote control, computer device, smart phone, and/or other remote monitor) such that the remote user provides commands to the drone through a wireless communications link to perform actions. More advanced drones are also being developed that are more autonomous (e.g., fully autonomous, semi-autonomous) such that drone guidance systems may assist the remote user or remove the need for the remote user altogether. These fully autonomous drones may be configured to follow an individual or group of individuals or monitor a location where individuals may be present.

SUMMARY

Drone-based data collection systems and methods are described. In some embodiments, an unmanned aerial vehicle, or drone, includes a plurality of sensors, including an imaging sensor, a communications interface, and a memory storing identity data associated with one or more users and observation data associated with the one or more users. The drone may navigate to an area including one or more individuals, and obtain, using a subset of the sensors including the imaging sensor, sensor data corresponding to the individuals. The drone may determine, based on the obtained sensor data and the identity data, that one of the individuals corresponds to identity data of a user stored in the memory. The drone may further determine that the user corresponding to the identity data requires medical assistance, using another subset of sensors. The drone may further transmit, to a third party, health data associated with the user corresponding to the identity data, which may be used to assist the third party in administering care to the user.

In various embodiments of the systems and methods disclosed herein, the plurality of sensors includes an acoustic sensor.

In various embodiments of the systems and methods disclosed herein, the plurality of sensors includes a biometric sensors.

In various embodiments of the systems and methods disclosed herein, the drone also includes an acoustic emitter, and the drone audibly emits, using the emitter, care instructions associated with the user corresponding to the identity data.

In various embodiments of the systems and methods disclosed herein, the user is a first user, and the drone processes sensor data captured by an acoustic sensor from a second user to determine that the first user requires medical assistance.

In various embodiments of the systems and methods disclosed herein, the drone determines that the user requires medical assistance by processing data received by the communications interface of the drone.

In various embodiments of the systems and methods disclosed herein, the drone determines, based on image sensor data, the sensors to be used in determining whether the user requires medical assistance.

Figure 1:
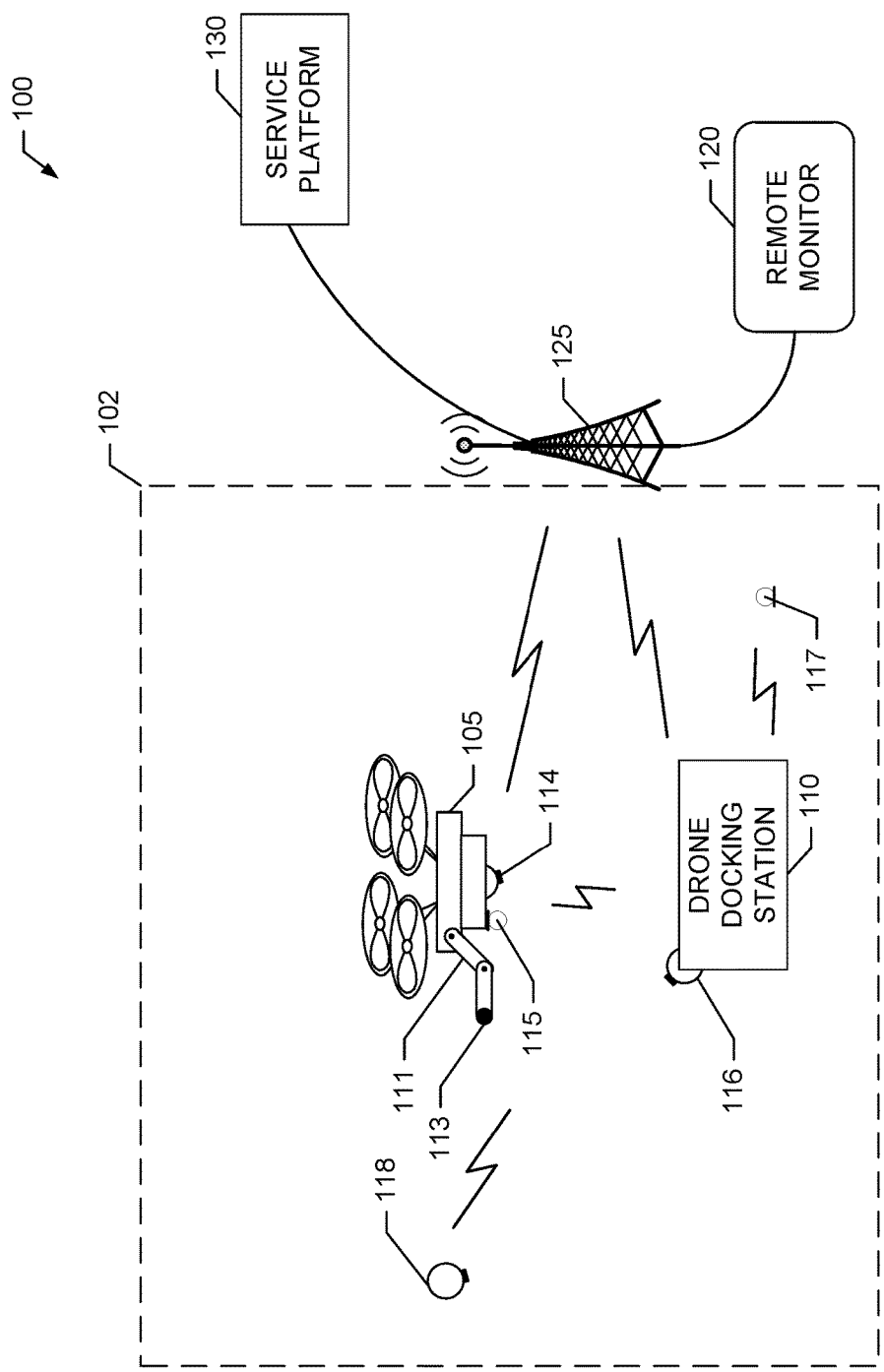
FIG. 1 is a schematic view illustrating an embodiment of a drone data storage system.

Embodiments of the present disclosure may be understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

Embodiments of the present disclosure include drone data locker systems and methods that may be used, for example, to continually collect and store observation data on an observed subject, such as an individual, group of individuals, animal, stationary object, moving object, and the like. As discussed above, some autonomous drones may be configured to follow an individual or group of individuals, or monitor a location where individuals may be present. Alternatively, some autonomous drones may be configured to navigate to be proximate to one or more individuals. Utilizing one or more sensors deployed on the autonomous drones, a drone may obtain sensor data corresponding to one or more individuals, and determine, based on the obtained sensor data, that the individual or individuals correspond to identity data of a user stored in the drone's memory. Further, utilizing one or more sensors deployed on the autonomous drones, the drone may determine that the user corresponding to the identity data requires medical assistance. Responsive to the determination, the drone may access stored health data associated with the user corresponding to the identity data and provide the health data to medical personnel or another user. Therefore, it may be beneficial for a drone to be configured to determine an individual's identity, and access health data which may be used to assist the individual in times of necessity.

The systems and methods of the present disclosure provide for a drone data storage system that includes a drone that can be dispatched and autonomously navigated to investigate an individual within a monitored space when a condition exists to do so. In addition, the drone can continually monitor an individual within a monitored space upon request by the individual or a third party. Once the drone is within a predefined range of the individual and/or while the drone is in-flight toward the individual, the drone may determine, based on sensor data, whether the individual corresponds to a stored identity. The drone may further determine whether the individual requires a service, such as health assistance, based on the conditions within the monitored space and the individual.

Referring now to FIG. 1, an embodiment of a drone data storage system 100 is illustrated. In the illustrated embodiment, the drone data storage system 100 includes a drone 105 provided in a monitored space 102. The monitored space 102 may be any indoor and/or outdoor or outside space that may be contiguous or non-contiguous. The monitored space 102 may be defined by geofencing techniques that may include specific geographic coordinates such as latitude, longitude, and/or altitude, and/or operate within a range defined by a wireless communication signal.

The drone 105 may be implemented by any type of drone, such as an unmanned aerial vehicle (UAV). In alternative embodiments, a robot, an unmanned vehicular device (e.g., land or water), and/or other vehicular device may be employed. In the illustrated examples of the present disclosure, the drone 105 is depicted as a UAV and includes a flight control unit and a payload unit. For example, the flight control unit of the drone 105 includes any appropriate avionics, control actuators, and/or other equipment to fly the drone. The payload unit of the drone 105 includes any equipment implementing features supported by the given drone. For example, the payload unit may include one or more sensors, such as one or more cameras and/or other imaging sensors 114, one or more environmental sensors (e.g., such as one or more temperature sensors, pressure sensors, humidity sensors, gas sensors, altitude sensors, location sensors and the like) and/or any other sensor. In the illustrated embodiment, the drone 105 may include an acoustic sensor 115 (e.g., a microphone, a microphone array, a directionally-discriminating acoustic sensor/transducer, and other acoustic sensors for detecting acoustic energy). Additionally or alternatively, an example payload unit for the drone 105 may include tools, actuators, manipulators, etc., capable of manipulating (e.g., touching, grasping, delivering, measuring, etc.) objects. For example, as illustrated in FIG. 1, the drone may include a robotic arm 111 that is configured to deploy the one or more sensors include on the robotic arm 111. For example, the one or more sensors included on the robotic arm 111 may include one or more sensors discussed above and/or a biometric sensor 113. The biometric sensor 113 may include an ocular sensor (e.g., a retinal scanner, an iris scanner, and/or other ocular sensor), a fingerprint sensor, a blood type sensor, a DNA sensor, a temperature sensor, a blood pressure sensor, a heartbeat sensor, and/or other biometric sensors. Additionally or alternatively, an example payload unit for the drone 105 may include a portable base station, signal booster, signal repeater, etc., to provide network coverage to an area.

The drone data storage system 100 may optionally include or be used in connection with a drone docking station 110 for drone launching, landing, and/or storing the drone 105. The drone docking station 110 may be located anywhere in the monitored space 102 such as a rooftop, a yard, a vehicle, a room, or elsewhere. The drone docking station 110 may be connected to an external power grid and/or receive power from a local power source such as wind, solar, and/or thermal and store this power in one or more power supplies such as batteries. In certain embodiments, a battery of the drone 105 may be charged by the drone docking station 110 through a conduction pad and/or through an inductive charging device using the power of the drone docking station 110. The drone docking station 110 may include one or more sensors 116 such as one or more cameras and/or other imaging sensors, acoustic sensors, biometric sensors, one or more environmental sensors described above, and/or other sensors. Furthermore, the drone docking station 110 may include an autonomous docking guidance system for guiding the drone 105 to dock with the drone docking station 110. For example, the drone docking station 110 may include at least one visual indicator (e.g., lights, reflectors) and/or acoustic indicators that are recognizable by the drone 105 to assist the drone 105 in docking with the drone docking station 110.

The drone 105 and the drone docking station 110 may include communication units having one or more transceivers to enable the drone 105 to communicate with the drone docking station 110, one or more sensors 117 and 118 located in the monitored space 102, a remote monitor 120, a service platform 130, and/or to communicate among other drones. The drone 105 and the drone docking station 110 may also communicate with one or more "smart" devices (also referred to as Internet of Things (IoT) devices) located in the monitored space 102 or outside of the monitored space 102. For example, IoT devices may include thermostat devices within a monitored space, occupancy sensors within a monitored space, appliances (e.g., refrigerators), or other such devices. Accordingly, and as disclosed in further detail below, the remote monitor 120 may be in communication with the drone 105 directly or indirectly. As used herein, the phrase "in communication," including variances thereof, encompasses direct communication and/or indirect communication through one or more intermediary components and does not require direct physical (e.g., wired and/or wireless) communication and/or constant communication, but rather additionally includes selective communication at periodic or aperiodic intervals, as well as one-time events.

For example, the drone 105 and/or the drone docking station 110 in the drone data storage system 100 of FIG. 1 include first (e.g., long-range) transceiver(s) to permit the drone 105 and/or the drone docking station 110 to communicate with a communication network 125. The communication network 125 may be implemented by an example mobile cellular network, such as a long term evolution (LTE) network or other third generation (3G), fourth generation (4G) wireless network, or fifth-generation (5G) wireless network. However, in some examples, the communication network 125 may be additionally or alternatively be implemented by one or more other communication networks, such as, but not limited to, a satellite communication network, a microwave radio network, and/or other communication networks. In other examples, the drone docking station 110 may maintain a network connection through a wired (e.g., Ethernet) connection.

The drone 105 and the drone docking station 110 additionally or alternatively may include second (e.g., short-range) transceiver(s) to permit the drone 105 and/or the drone docking station 110 to communicate with each other, the sensors 117 and 118, other drones and/or other drone docking stations. In the illustrated example of FIG. 1, such second transceivers are implemented by a type of transceiver supporting short-range wireless networking. For example, such second transceivers may be implemented by Wi-Fi transceivers, Bluetooth® transceivers, infrared (IR) transceiver, and other transceivers that are configured to allow the drone 105 and/or the drone docking station 110 to intercommunicate via an ad-hoc or other wireless network.

The drone data storage system 100 also includes or may be used in connection with a remote monitor 120. The remote monitor 120 may be provided by a desktop computing system, a laptop/notebook computing system, a tablet computing system, a mobile phone, a set-top box, a remote control, a wearable device, and implantable device, and/or other remote monitor for controlling drones. The remote monitor 120 may be responsible for managing the drone 105 deployed in the monitored space 102. For example, the remote monitor 120 may communicate directly through the communication network 125 and/or indirectly through the drone docking station 110 to locate the drone 105 in the monitored space 102, identify the drone 105 in the monitored space 102, ascertain capabilities of the drone 105 in the monitored space 102, monitor the operating status of the drone 105 in the monitored space 102, receive sensor data provided by the drone 105 in the monitored space 102, provide instructions to the drone 105, and/or provide other functionality.

The drone data storage system 100 also includes or may be in connection with a service platform 130. For example, the service platform 130 may include one or more server devices, storage systems, cloud computing systems, and/or other computing devices (e.g., desktop computing device(s), laptop/notebook computing device(s), tablet computing device(s), mobile phone(s), etc.). As discussed below, the service platform 130 may be configured to provide repositories such a user repository of user profiles and a service repository of service profiles. For example, the user repository may include a plurality of user profiles that are associated with a user of the drone and/or a service that is accessible via the drone. The service repository may include a plurality of service profiles that the service platform monitors to determine whether a condition in the monitored space exists, such as a health-related condition of a monitored user. Also, as discussed below, the service platform 130 may be configured to provide a verification engine that verifies that an individual is a user of the drone and/or service being accessed via the drone. The service platform may also include and services engine for communicating instruction to the drone 105 to provide a service.

Figure 2:
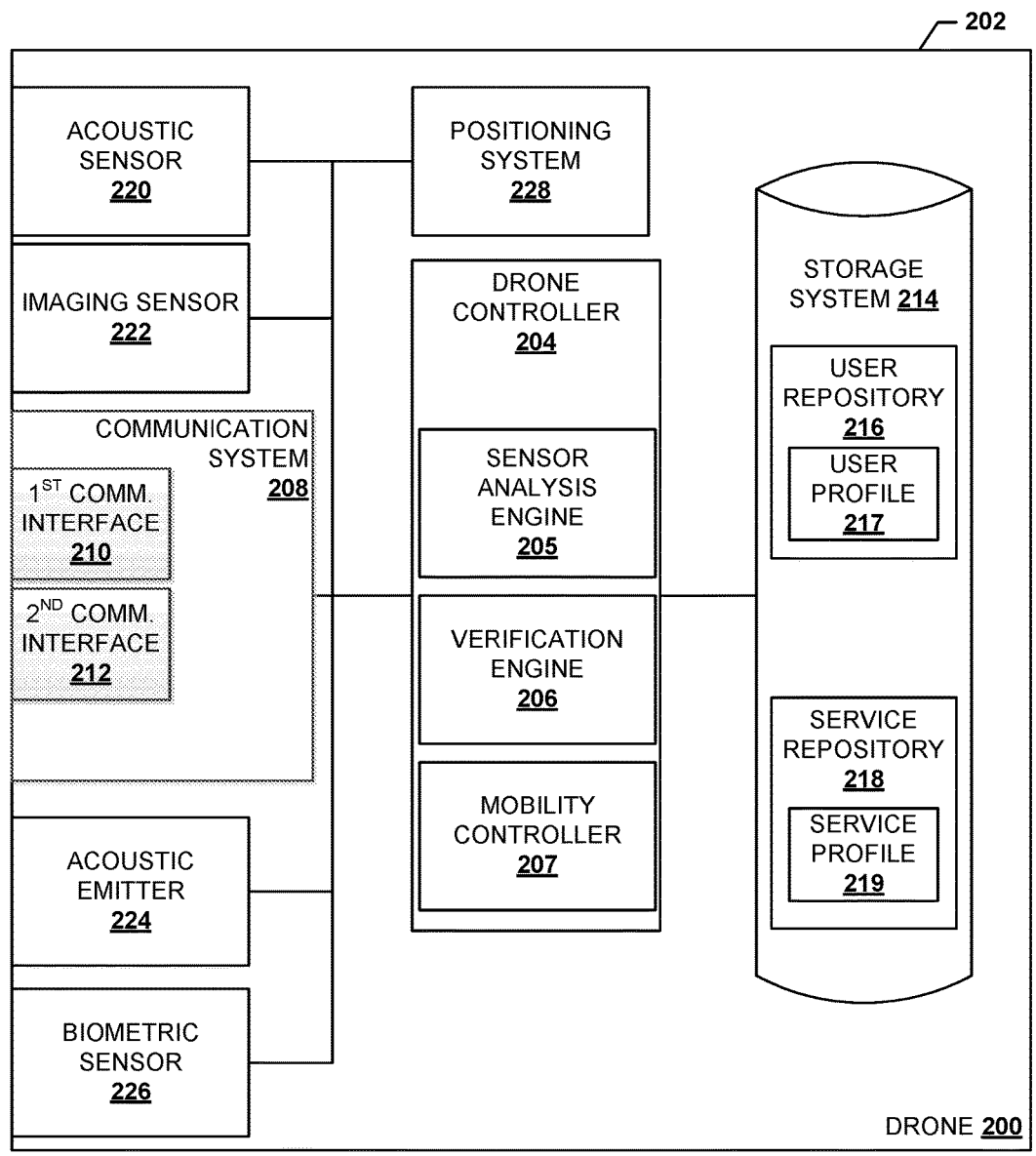
FIG. 2 is a schematic view illustrating an embodiment of a drone used in the drone data storage system of FIG. 1.

Referring now to FIG. 2, an embodiment of a drone 200 is illustrated that may be the drone 105 discussed above with reference to FIG. 1, and which may be provided by a UAV, a robot, an unmanned vehicular device (e.g., land or water), and/or other vehicular device. In the illustrated embodiment, the drone 200 includes a chassis 202 that houses the components of the drone 200. Several of these components are illustrated in FIG. 2. For example, the chassis 202 may house a processing system (not illustrated) and a non-transitory memory system (not illustrated) that includes instructions that, when executed by the processing system, cause the processing system to provide a drone controller 204 that is configured to perform the functions of the drone controllers and/or the drones discussed below. In the specific example illustrated in FIG. 2, the drone controller 204 is configured to provide a sensor analysis engine 205 that computationally processes sensor signals with stored sensor signal profiles, and a verification engine 206 that performs identification of a user as well as the functionality discussed below. In the specific example illustrated in FIG. 2, the drone controller 204 is also configured to provide a mobility controller 207 to control the example flight control unit of drone 105 and to implement any control and feedback operations appropriate for interacting with avionics, control actuators, and/or other equipment included in the flight control unit to navigate the drone 105 illustrated in FIG. 1.

The chassis 202 may further house a communication system 208 that is coupled to the drone controller 204 (e.g., via a coupling between the communication system 208 and the processing system). The communication system 208 may include software or instructions that are stored on a computer-readable medium and that allow the drone 200 to send and receive information through the communication networks discussed above. For example, the communication system 208 may include a first communication interface 210 to provide for communications through the communication network 125 as detailed above (e.g., first (e.g., long-range) transceiver(s)). In an embodiment, the first communication interface 210 may be a wireless antenna that is configured to provide communications with IEEE 802.11 protocols (Wi-Fi), cellular communications, satellite communications, other microwave radio communications and/or communications. The communication system 208 may also include a second communication interface 212 that is configured to provide direct communication with other drones, the drone docking station 110, sensors 117 and 118, the remote monitor 120, and/other devices within the monitored space 102 discussed above with respect to FIG. 1 (e.g., second (e.g., short-range) transceiver(s)). For example, the second communication interface 212 may be configured to operate according to wireless protocols such as Bluetooth®, Bluetooth® Low Energy (BLE), near field communication (NFC), infrared data association (IrDA), ANT®, Zigbee®, Z-Wave® IEEE 802.11 protocols (Wi-Fi), and other wireless communication protocols that allow for direct communication between devices.

The chassis 202 may also house a storage system 214 that is coupled to the drone controller 204 through the processing system. The storage system 214 may store user profiles 217 in one or more user repositories 216. The user profiles 217 may include information associated with a user of the drone 200 and/or a service provided by the drone 200. For example, a user profile 217 may include a user identifier that is associated with the user or associated with a user of a service. For example, the user identifier may include a username, a phone number, an electronic mail address, a user device identifier (e.g., a communication interface identifier of a mobile device) and/or other identifiers that can identify the user. Each user identifier may have user information associated with the user identifier that can be used by the drone 200 to undertake various services. For example, the user information may include preselected preferences, third party data, gathered data by the drone data storage system 100 over time, identity data such as sensor signal profiles (e.g., an acoustic profile, an image profile (e.g., an image profile which can be used for facial recognition techniques), a blood profile, a DNA profile, a fingerprint profile, an ocular profile and/or other sensor signal profile that can be used to identify the individual and be updated from gathered data over time using machine learning techniques discussed below), and/or any other data used for verifying an individual as a user and providing services to that user, such as accessing health data for the user. Medical or health records stored by the storage system 214 may be stored in compliance with applicable laws and regulations, e.g., the Health Insurance Portability and Accountability Act (HIPAA), and may also be encrypted as appropriate. The user information may be collected over a period of time in which the drone has been associated with the user. In some embodiments, user information may be stored for multiple users, such as a family or group of users, in data repository 216. In some embodiments, user information may be stored for a group of users as individual user profiles 217, or as a singular user profile 217. In addition, the storage system 214 may include a service repository 218 that includes a plurality of service profiles 219. The service repository 218 may include at least one application that provides instruction to the drone controller 204 when at least one condition is satisfied in a monitored space. In addition the at least one application may require that an individual in the monitored space to be verified as a user before providing the service. Each application may be associated with service profile 219 that includes sensor signal profiles of conditions that need to be satisfied before the application associated with that service profile 219 can be run on the drone controller 204. In one example, the service repository 218 may include a service profile 219 that instructs the drone 200 to communicate with medical personnel upon detection of a health condition of a verified user.

The chassis 202 may also house an acoustic sensor 220 (e.g., a microphone, a microphone array, a directionally-discriminating acoustic sensor, or other acoustic sensors), an imaging sensor 222 (e.g., a two-dimensional image capturing camera, a three-dimensional image capturing camera, an infrared image capturing camera, a depth capturing camera, similar video recorders, and/or a variety of other image or data capturing devices), a biometric sensor 226 (an ocular sensor, a fingerprint sensor, a blood type sensor, a DNA sensor, a temperature sensor, a blood pressure sensor, a heartbeat sensor, and other biometric sensors) and in some embodiments, an acoustic emitter 224.

For example, the acoustic sensor 220 may include an microphone array that is configured to capture audio signals from acoustic energy in a monitored space and provide the audio signals to the sensor analysis engine 205 and/or verification engine 206 to computationally process the audio signals against acoustic profiles associated with the user profiles 217 and/or service profiles 219 that are stored in the storage system 214 to determine whether substantial correspondence with any of the acoustic profiles exists. The acoustic sensor 220 may also be used to determine an apparent direction and/or location of the apparent source that provided the acoustic energy as discussed further below. Similarly, the acoustic emitter 224 may include a speaker array or other sound emitting device that generates and emits acoustic energy to the monitored space such that the acoustic energy is reflected off objects within the monitored space. Those objects then become apparent sources of the acoustic energy that provide unique reflected acoustic energy back to the acoustic sensor 220. Further, the acoustic sensor 220 may be configured to provide audio signals to the sensor analysis engine 205 to computationally process the audio signals to perform speech recognition capabilities to determine whether an individual's speaking or voice indicates a need for medical assistance.

The imaging sensor 222 may be a camera and/or any other sensor device that may be used to gather visual information from the monitored space surrounding the drone 200 for use in verifying that an individual is a user of the drone, determining that an individual requires medical assistance, and/or identifying and providing a service with the drone 200. Imaging sensor signals may be provided to the sensor analysis engine 205 and/or verification engine 206 to computationally process the imaging sensor signals against image profiles associated with the user profiles 217 and/or service profiles 219 that are stored in the storage system 214 to determine whether substantial correspondence with any of the image profiles exists. Similarly, the biometric sensors 226 other than the acoustic sensor 220 and the imaging sensor 222 may be used to gather biometric data from an individual in the monitored space 102 for use in verifying the individual, determining whether the individual requires medical assistance, and/or identifying and providing a service with the drone 200. Biometric sensor signals may be provided to the sensor analysis engine 205 and/or verification engine 206 to computationally process the biometric sensor signals against biometric profiles associated with the user profiles 217 and/or service profiles 219 that are stored in the storage system 214 to determine whether substantial correspondence with any of the biometric profiles exists, or to determine whether an individual requires medical assistance. The biometric sensors 226 may also include a deployable remote sensor which can be removed from the drone 200 to collect data, and reattached or reinstalled on the drone 200 at a later time. The deployable remote sensor may also be disposable and not later reattached or reinstalled.

The drone 200 may also include a positioning system 228 that is coupled to the drone controller 204. The positioning system 228 may include sensors for determining the location and position of the drone in the monitored space. For example the positioning system 228 may include a global positioning system (GPS) receiver, a real-time kinematic (RTK) GPS receiver, a differential GPS receiver, a Wi-Fi based positioning system (WPS) receiver, an accelerometer, and/or other positioning systems and components.

Figure 3:
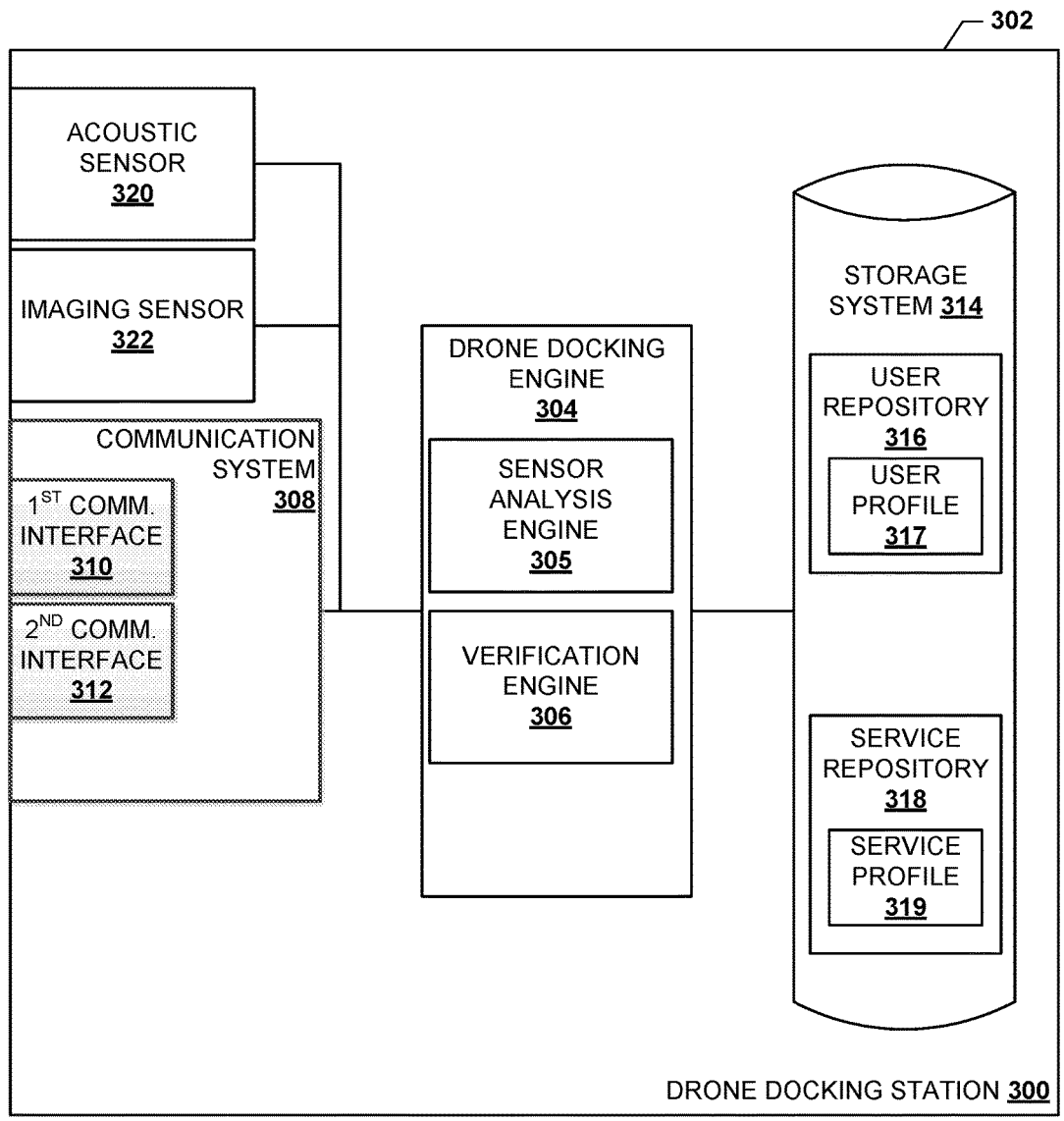
FIG. 3 is a schematic view illustrating an embodiment of a drone docking station used in the drone data storage system of FIG. 1.

Referring now to FIG. 3, an embodiment of a drone docking station 300 is illustrated that may be the drone docking station 110 discussed above with reference to FIG. 1. In the illustrated embodiment, the drone docking station 300 includes a chassis 302 that houses the components of the drone docking station 300. Several of these components are illustrated in FIG. 3. For example, the chassis 302 may house a processing system (not illustrated) and a non-transitory memory system (not illustrated) that includes instructions that, when executed by the processing system, cause the processing system to provide a drone docking engine 304 that is configured to perform the functions of the drone docking engines and/or the drone docking stations discussed below. In the specific example illustrated in FIG. 3, the drone docking engine 304 is configured to provide a sensor analysis engine 305 that computationally processes sensor signals against stored sensor signal profiles, and an verification engine 306 that performs verification of a user as well as the functionality discussed below.

The chassis 302 may further house a communication system 308 that is coupled to the drone docking engine 304 (e.g., via a coupling between the communication system 308 and the processing system). The communication system 308 may include software or instructions that are stored on a computer-readable medium and that allow the drone docking station 300 to send and receive information through the communication networks discussed above. For example, the communication system 308 may include a first communication interface 310 to provide for communications through the communication network 125 as detailed above (e.g., first (e.g., long-range) transceiver(s)). In a specific example, the first communication interface 310 may be a wireless antenna that is configured to provide communications with IEEE 802.11 protocols (Wi-Fi), cellular communications, satellite communications, other microwave radio communications and/or communications. In other examples, the first communication interface 310 may provide wired communications (e.g., Ethernet protocol) from the drone docking station 300 through the communication network 125. The communication system 308 may also include a second communication interface 312 that is configured to provide direct communication with the drone 105, other drone docking stations, sensors (e.g., sensors 117 and 118), monitors, and/other devices within the monitored space 102 discussed above with reference to FIG. 1 (e.g., second (e.g., short-range) transceiver(s)). For example, the second communication interface 312 may be configured to operate according to wireless protocols such as Bluetooth®, Bluetooth® Low Energy (BLE), near field communication (NFC), infrared data association (IrDA), ANT®, Zigbee®, Z-Wave® IEEE 802.11 protocols (Wi-Fi), and other wireless communication protocols that allow for direct communication between devices.

The chassis 302 may also house a storage system 314 that is coupled to the drone docking engine 304 through the processing system and that is configured to store the rules and/or other data utilized by the drone docking engine 304 to provide the functionality discussed below. The storage system 314 may store user profiles 317 in one or more user repositories 316. The user profiles 317 may include information associated with a user of the drone data storage system 100 and/or a service provided by the drone 200. For example, a user profile 317 may include a user identifier that is associated with the user. For example, the user identifier may include a username, a phone number, an electronic mail address, a user device identifier (e.g., a communication interface identifier of a mobile device) and/or other identifiers that can identify the user. Each user identifier may have user information associated with the user identifier that can be used by the drone data storage system 100 to undertake various services. For example, the user information may include preselected preferences, third party data, gathered data by the drone data storage system 100 over time, identity data such as sensor signal profiles (e.g., an acoustic profile, an image profile, a blood profile, a DNA profile, a fingerprint profile, an ocular profile and/or other sensor signal profile that can be used to identify the individual and be updated from gathered data over time using machine learning techniques discussed below), and/or any other data used for verifying an individual as a user of a drone or drone service and providing services to that user. In addition, the storage system 314 may include a service repository 318 that includes a plurality of service profiles 319. The service repository 318 may include one or more applications that provide instruction to the drone controller 204 and/or drone docking engine 304 when one or more conditions are satisfied in the monitored space and/or that may need an individual in the monitored space to be verified as a user. Each application may be associated with service profile 319 that includes sensor signal profiles of conditions that need to be satisfied before the application associated with that service profile can be run on the drone controller 204 and/or drone docking engine 304.

The chassis 302 may also house an acoustic sensor 320 (e.g., a microphone, a microphone array, a directionally-discriminating acoustic sensor, and other acoustic sensors), an imaging sensor 322 (e.g., a two-dimensional image capturing camera, a three-dimensional image capturing camera, an infrared image capturing camera, a depth capturing camera, similar video recorders, and/or a variety of other image or data capturing devices), and in some embodiments, an acoustic emitter and a biometric sensor (not illustrated).

For example, the acoustic sensor 320 may include an microphone array that is configured to capture audio signals from acoustic energy in a monitored space and provide the audio signals to the sensor analysis engine 305 and/or verification engine 306 to computationally process the audio signals against acoustic profiles associated with the user profiles 317 and/or service profiles 319 that are stored in the storage system 314 to determine whether substantial correspondence with any of the acoustic profiles exists. The acoustic sensor 320 may also be used to determine an apparent direction and/or location of the apparent source that provided the acoustic energy as discussed further below.

The imaging sensor 322 may be a camera and/or any other sensor device that may be used to gather visual information from the monitored space surrounding the drone docking station 300 for use in verifying an individual as a user of a drone or drone service and/or identifying and providing a service with the drone docking station 300. Imaging sensor signals may be provided to the sensor analysis engine 305 and/or verification engine 306 to computationally process the imaging sensor signals against image profiles associated with the user profiles 317 and/or service profiles 319 that are stored in the storage system 314 to determine whether substantial correspondence with any of the image profiles exists.

Figure 4:
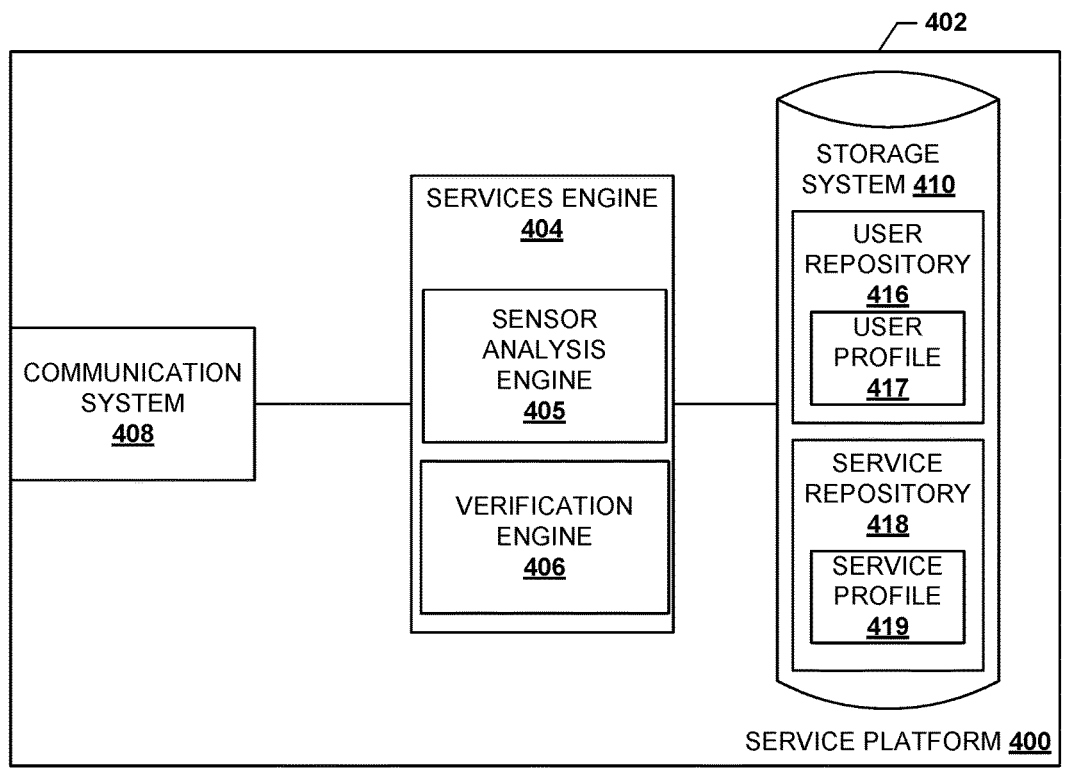
FIG. 4 is a schematic view illustrating an embodiment of a service platform used in the drone data storage system of FIG. 1.

Referring now to FIG. 4, an embodiment of a service platform 400 is illustrated that may be the service platform 130 discussed above with reference to FIG. 1. In the illustrated embodiment, the service platform 400 includes a chassis 402 that houses the components of the service platform 400, only some of which are illustrated in FIG. 4. For example, the chassis 402 may house a processing system (not illustrated) and a non-transitory memory system (not illustrated) that includes instructions that, when executed by the processing system, cause the processing system to provide a services engine 404 that is configured to perform the functions of the services engines and/or service provider devices discussed below. In the specific example illustrated in FIG. 4, the services engine 404 is configured to provide a sensor analysis engine 405 that computationally processes sensor signals against stored sensor signal profiles, and an verification engine 406 that performs verification of a user as well as the functionality discussed below.

The chassis 402 may further house a communication system 408 that is coupled to the services engine 404 (e.g., via a coupling between the communication system 408 and the processing system) and that is configured to provide for communication through the network as detailed below. The communication system 408 may allow the service platform 400 to send and receive information over the communication network 125 of FIG. 1. The chassis 402 may also house a storage system 410 that is coupled to the services engine 404 through the processing system and that is configured to store the rules and/or other data utilized by the services engine 404 to provide the functionality discussed below. The storage system 410 may store user profiles 417 in one or more user repositories 416. The user profiles 417 may include information associated with a user of the drone data storage system 100 and/or a service provided by the drone 105/200 and/or service platform 400. For example, a user profile 417 may include a user identifier that is associated with the user. For example, the user identifier may include a username, a phone number, an electronic mail address, a user device identifier (e.g., a communication interface identifier of a mobile device) and/or other identifiers that can identify the user. Each user identifier may have user information associated with the user identifier that can be used by the drone data storage system 100 to undertake various services. For example, the user information may include preselected preferences, third party data, gathered data by the drone data storage system 100 over time, identity data such as sensor signal profiles (e.g., an acoustic profile, an image profile, a blood profile, a DNA profile, a fingerprint profile, an ocular profile and/or other sensor signal profile that can be used to identify the individual and be updated from gathered data over time using machine learning techniques discussed below), and/or any other data used for verifying an individual as a user, determining whether an individual requires medical assistance, and providing services to that user. In addition, the storage system 410 may include a service repository 418 that includes a plurality of service profiles 419. The service repository 418 may include one or more applications that provide instruction to the services engine 404 and/or drone controller 204 when one or more conditions are satisfied in the monitored space and that may need an individual in the monitored space to be verified as a user. Each application may be associated with service profile 419 that includes sensor signal profiles of conditions that need to be satisfied before the application associated with that service profile can be run on the drone controller 204 and/or services engine 404.

Figure 5:
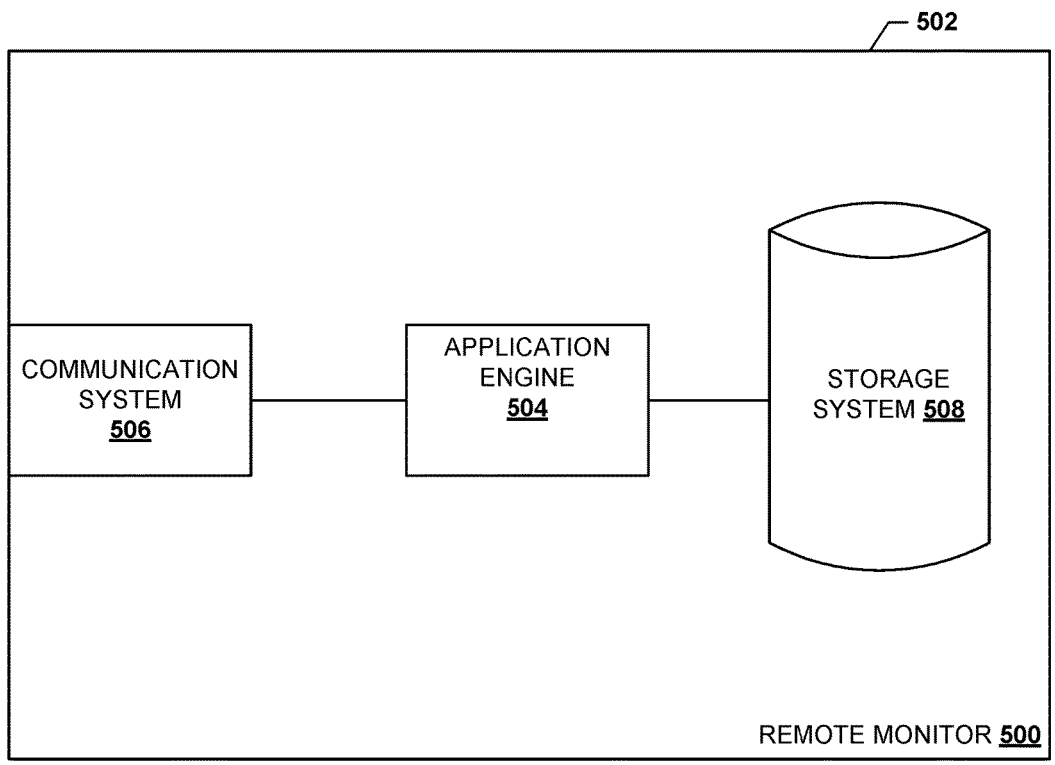
FIG. 5 is a schematic view illustrating an embodiment of a remote monitor used in the drone data storage system of FIG. 1.

Referring now to FIG. 5 an embodiment of a remote monitor 500 is illustrated that may be the remote monitor 120 discussed above with reference to FIG. 1. In the illustrated embodiment, the remote monitor 500 includes a chassis 502 that houses the components of the remote monitor 500. Several of these components are illustrated in FIG. 5. For example, the chassis 502 may house a processing system (not illustrated) and a non-transitory memory system (not illustrated) that includes instructions that, when executed by the processing system, cause the processing system to provide an application engine 504 that is configured to perform the functions of the application engines, drone applications, and/or remote monitors discussed below. In the specific example illustrated in FIG. 5, the application engine 504 is configured to receive notifications from a drone and/or drone docking station that include audio feeds and video feeds, provide those notifications to an user through a drone application, receive instructions from the user through the drone application, and provide those instructions over a communication network to the drone and/or drone docking station as well as the functionality discussed below.

The chassis 502 may further house a communication system 506 that is coupled to the application engine 504 (e.g., via a coupling between the communication system 506 and the processing system) and that is configured to provide for communication through the network as detailed below. The communication system 506 may allow the remote monitor 500 to send and receive information over the communication network 125 of FIG. 1. The chassis 502 may also house a storage system 508 that is coupled to the application engine 504 through the processing system that is configured to store the rules, graphics, and/or other data utilized by the application engine 504 to provide the functionality discussed below. While the storage system 508 has been illustrated as housed in the chassis 502 of the remote monitor 500, one of skill in the art will recognize that the storage system 508 may be connected to the application engine 504 through the communication network 125 via the communication system 506 without departing from the scope of the present disclosure.

In some embodiments, drones within the drone data storage system have a one-to-one relationship with an observed subject. For example, a single drone may be associated with a single human person. In some embodiments, drones within the drone data storage system have a one-to-many relationship with observed subjects; for example, a single drone may serve a family, group, or other collection of users. In some embodiments, a single drone may always be associated with its observed subject or subjects. For example, a human user may purchase a drone to be used to monitor and collect data for an elderly relative. In some embodiments, a single drone may, on a subscription basis, be used to monitor and collect data on a subject. For example, a drone-sharing arrangement may be employed in which a drone navigates itself for a set amount of time to observe a particular subject, and once that amount of time expires, the drone may navigate itself to another subject to perform the same observation and collection of data. In some embodiments, a drone may be dispatched on-demand to observe, monitor, and collect data on a subject; for example, responsive to an event occurring, a drone may be dispatched to autonomously observe and collect data on a subject. In some embodiments, the drone may verify that a user is a user of a drone service or drone-sharing arrangement before collecting data on the user. The drone may be dispatched in response to a command from a user, or may be automatically dispatched in response to a signal by a remote monitor (such as remote monitor 120).

Figure 6:
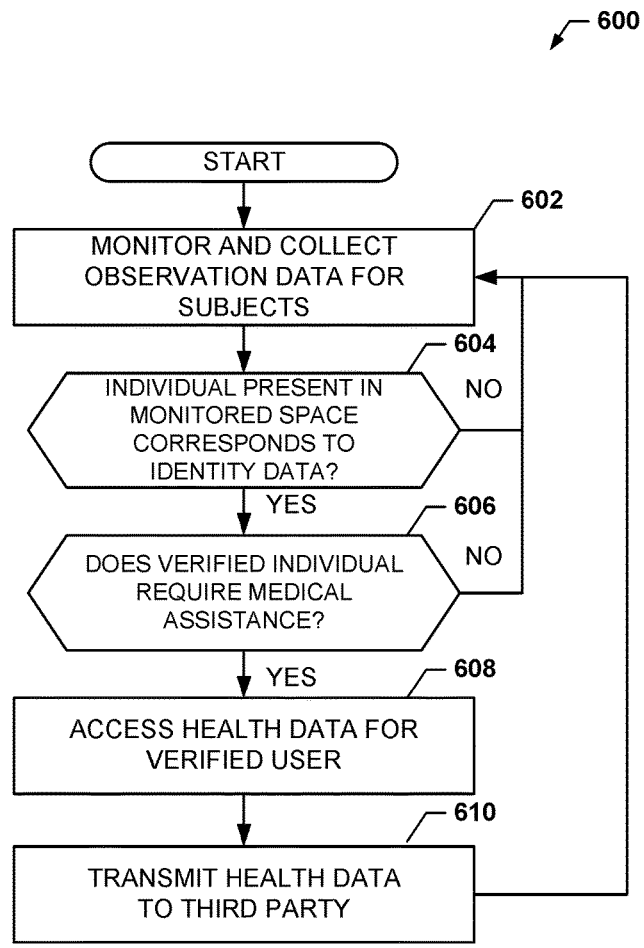
FIG. 6 is a flow chart illustrating an embodiment of a method of storage and analysis of data using one or more drones.

Referring now to FIG. 6, an embodiment of a method 600 for determining whether a subject requires assistance is illustrated. As discussed below, the systems and methods of the present disclosure provide a drone data storage system that includes a drone and optionally a drone docking station that continually collects and stores observation data on observed objects, such as individuals in a monitored space, in some embodiments to determine whether an individual requires medical assistance. The drone data storage system may include a drone that can collect data and facilitate the provision of various services and/or provision of various interactions with individuals such as humans, animals (e.g., livestock, pets, and wildlife), and plants (e.g., trees and crops) and/or other identifiable objects (e.g., fences, buildings, vehicles, other drones). When providing services to individuals, the drone data storage system may require that the individual is verified to be an individual associated with identity data stored in a drone or accessible to the drone, based on sensor data collected or obtained by the drone. Furthermore, the drone data storage system may require that an individual is determined to be in need of assistance (for example, medical assistance), based on an additional set of sensor data collected or obtained by the drone. The systems and methods of the present disclosure assess a monitored space, in which an individual requiring a service is located, to verify or determine whether any such individual is a user of the drone and requires medical assistance. The drone, or another component of the drone data storage system, then captures sensor signals from additional sensors that can be used to determine the type of medical assistance required and, if needed, communicate with other devices to notify additional users of the situation or request medical assistance from medical personnel. These systems and methods provide a drone with the ability to provide or facilitate provision of medical services to individuals in situations where the drone has access to the individual's health data.

The method 600 begins at block 602 where a drone monitors and collects observation data for a subject, such as an individual. As discussed previously, an autonomous drone may be configured to follow an individual and using one or more sensors, obtain, collect, and store sensor data for the individual. In an embodiment, at block 602 and with reference to the drone data storage system 700 of FIG. 7, the drone 105/200 and/or the drone docking station 110/300 may be in a monitoring mode, also referred herein as a standby mode, and collect data related for one or more individuals 705 (e.g., a human, an animal, and/or other living thing) in a monitored space 102 (e.g., a yard, a home, a business, a park, a stadium, a transmission line area, an access space, underground shafts, or other spaces). The monitored space 102 may be contiguous or non-contiguous. The monitored space 102 may be defined by geofencing techniques that may include specific geographic coordinates such as latitude, longitude, and/or altitude, and/or operate within a range defined by a wireless communication signal. In one embodiment, the drone 105/200 may be deployed to a location in which one or more individuals are present; for example, the drone may be provided with navigation coordinates for a location, and autonomously navigate to the location.

In one embodiment, a drone obtains data from a subject on a periodic basis (e.g., once an hour, once a day, etc.). In one embodiment, a drone may obtain sensor data for a subject, and also receive other observation data for the subject from additional sources. For example, a drone may be authorized to access a subject's medical records from doctor's visits via a communication network. In one embodiment, accessing of medical records utilizes a secure method of communication, such as a virtual private network connection. Similarly, a drone may communicate with a device possessed by a subject, such as a mobile telephone, smart watch, or fitness band which transmits health data (e.g., pulse rate) to the drone. Other health-specific data obtained by a subject's device may also transmit health data to the drone; for example, a glucose monitor used by the subject may transmit periodic glucose readings to the drone. In one embodiment, data is obtained by a drone from a remote monitor 120 or service platform 130. Data may also be replicated between a drone 105 and other data storage devices. In one embodiment, one or more drones may be part of a service offered by a service provider which a subject may sign up for, and which the subject may instruct or request to continually monitor and collect his or her health data. That is, a service provider may provide a drone as a service, in which a plurality of drones are deployed which collect health data from users of the drone service. In such a service, a drone can potentially serve multiple subjects. Various drone-sharing models are contemplated, for example, in which a drone services multiple subjects which are all part of one family or one community, or in which a drone services only a single subject. Thus, in some embodiments, a drone may be instructed to navigate to one or more individuals who are part of, or have signed up for, a monitoring service. The drone may navigate to one or more individuals on a periodic basis to continually collect and update sensor data for the individual. In one embodiment, one or more users can sign up for the drone service on a subscription basis (e.g., with a fixed payment each month, week, or other time period). In one embodiment, one or more users may sign up for the drone service and be billed on a usage basis; for example, a first user may request that a drone collect observation data for a second user (e.g., a family member) for a day to ensure the second user's safety. Similarly, one or more users may sign up for the drone service on an event basis (e.g., a planned hike), such that the drone user may request that the drone collect observation data for himself or herself and be able to transmit information to a second user (e.g., a family member) in the event of an emergency the drone user encounters. In the event no emergency occurs, the drone may do nothing more than observe.

The drone 105/200 may include one or more sensors (e.g., an imaging sensor 114, a biometric sensor 113, and/or an acoustic sensor 115) that may generate sensor signals that can be collected and, optionally, computationally processed and stored within the drone. Likewise, the drone docking station 110/300 may include the sensor 116 that may generate sensor signals that can be collected and optionally computationally processed. In another example, the drone 105 and the drone docking station 110 may be coupled (e.g., wired and/or wirelessly) with sensors 117 and 118 that are dispersed throughout the monitored space 102 that may generate sensor signals that can be collected and computationally processed. The sensor signals can be processed by one or more of the sensor analysis engines 205, 305, and 405.

While in a monitoring mode, the drone 105/200 may be docked with the drone docking station 110. However, in other examples, the drone 105/200 may be at a monitor location or a standby location, the drone 105/200 may be proceeding along a patrol path within the monitored space 102, or at another monitoring position such as hovering in the monitored space 102. While the drone 105/200 and/or the drone docking station 110/300 is monitoring the monitored space 102, the drone 105/200 and/or the drone docking station 110/300 may be generating sensor signals and or receiving sensor signals from any of the sensors 113, 114, 115, 116, 117, and/or 118 in the monitored space 102. While the above example for block 602 of method 600 describes the drone 105/200 being in a monitoring mode when monitoring the monitored space, one skilled in the art in possession of the present disclosure will recognize that at block 602 the drone 105/200 may be in any other mode, such as in-flight mode, an investigate mode, or an assistive mode, as described further below, and still be monitoring the monitored space 102 for sensor signals.

Figure 7:
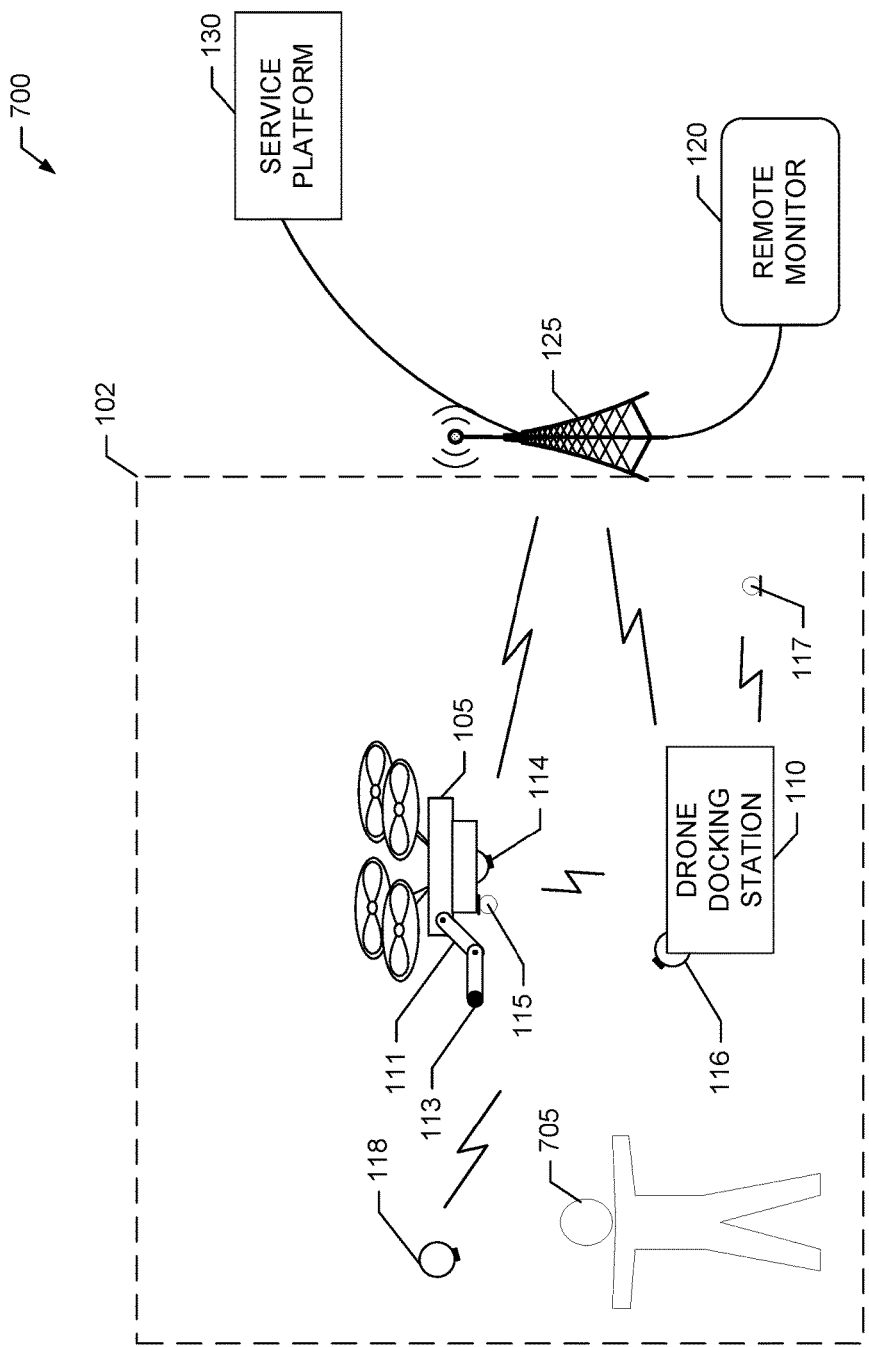
FIG. 7 is a schematic view illustrating an embodiment of the drone data storage system during the method of FIG. 6.

As shown in the example illustrated in FIG. 7, embodiments of the drone data storage system 700 are illustrated that include the drone data storage system 100 as illustrated in FIG. 1. As illustrated in FIG. 7, the drone data storage system 700 may be in a monitoring mode monitoring a monitored space 102 for an individual 705 in the monitored space 102 as described at block 602. In the illustrated example, the drone 105 may be hovering above the drone docking station 110 awaiting sensor signals captured by any of the sensors 113-118 that are in the monitored space 102. For example, the acoustic sensors 115 and 117 may be generating audio signals based on acoustic energy received at the acoustic sensors 115 and 117. The acoustic energy may be generated by an apparent source. For example, bird vocal cords may generate a "tweet" sound or a car horn when activated may generate a "honk" sound. In other examples, the acoustic energy may be reflected acoustic energy by an apparent source. For example, a communications wire transmission pole may reflect the sound of wind to provide acoustic energy and/or reflect acoustic energy generated from an acoustic emitter 224 such that reflected acoustic energy is received by the acoustic sensors 115 and 117. The imaging sensors 114, 116 and/or 118 may be generating digital images of the monitored spaces based on light radiation, infrared radiation, and other electromagnetic radiation. Data from such imaging sensors 114, 116, 118 may be analyzed using facial recognition techniques to determine the presence of an individual, verify the individual is a user of the drone's service, and collect data for that individual. In another example, the communication interfaces (e.g., communication interfaces 210, 212, 310, and/or 312) may be monitoring for wireless signals from user devices, which upon detection assumes a presence of an individual. The biometric sensor 113 may include a chemical sensor that can detect levels of carbon dioxide and/or include a microwave radar that may receive microwave radiation that may be computationally processed to detect a breathing pattern and/or a heartbeat of living things within the monitored space 102. Any sensor data gathered by one or more of the sensors 113-118 may be converted into sensor signals which include electrical signals that can be processed by the sensor analysis engine 205, 305, and/or 405 included in the drone data storage system 700.

The method 600 then proceeds to block 604 where it is determined whether an individual present in the monitored space corresponds to identity data stored by a monitoring drone, such as drone 105/200. In an embodiment, the determination at block 604 is performed on a periodic basis, for example, every five minutes. In an embodiment, the determination at block 604 is performed on an ad-hoc basis, such as when an individual enters the monitored space (as detected, for example, via sensor signals processed by the drone 105/200 or docking station 110/300). In an embodiment, the drone 105/200 may reposition itself or navigate itself into a different location to determine whether the individual corresponds to identity data stored by the drone. In one embodiment, block 604 may determine whether a non-living observed subject (e.g., a vehicle) corresponds to identity data stored by a monitoring drone for the object. In some embodiments, if the observed subject is a building, facility, or other non-moving object, the determination at block 604 may not be necessary.

In an embodiment, at block 604 the sensor signals generated by at least one of the sensors 113-118 are computationally processed against one or more individual presences profiles included in service profile 219, 319, and/or 419. In an embodiment, at block 604 the sensor analysis engine 205, 305, and/or 405 of the drone 105/200, drone docking station 110/300, and/or service platform 130/400 may computationally process the sensor signals received by the one or more sensors 113-118. The sensor analysis engine 205, 305, and/or 405 may determine whether any of the sensor signals have substantial correspondence with an individual presence profile stored in the respective user repositories 216, 316, and/or 416. A sensor signal profile described herein may be a digital summary of a sensor signal such as a sensor fingerprint that can be used to identify a sample of the sensor signal generated by one or more sensors that is obtained from the monitored space 102. For example, the individual presence profile may be a digital summary indicating an individual (e.g., a human and/or a specific animal). For example, the individual presence profile may include an acoustic profile of an individual. The acoustic profile may include feature vectors that define characteristics of an audio signal such as an average zero-crossing rate, average spectrum prominent tones across a set of frequency bands, estimated tempo, spectral flatness, bandwidth, and/or other audio signal features suitable for identifying audio signals. The acoustic profile may be associated with an apparent source identifier that identifies an apparent source that provides the acoustic profile, which may be an individual.

Sensor profiles, such as an acoustic profile of an individual presence profile, may also be configured such that any compression and/or encoding techniques (e.g., AAC, MP3, WMA, Vorbis, and other audio compression and/or encoding techniques) performed on the sensor signal to allow an acoustic analysis engine included on the sensor analysis engine 205, 305, and/or 405 to identify the sensor signal based on the sensor signal profiles. The sensor signals have substantial correspondence with a sensor signal profile when a predefined condition is satisfied. For example, the predefined condition may be that one or more feature vectors of the sensor signal match or are within a threshold of similarity (e.g., 50% similar, 60% similar, 70% similar, 80% similar, 85% similar, 90% similar, 95% similar, 99% similar, 100% similar and other thresholds of similarity) between the sensor signal and an sensor signal profile. Substantial correspondence may also include situations where unsupervised machined learning techniques (e.g., using cluster analysis), and/or supervised machine learning techniques (e.g., using statistical classification) determines that sensors signals in one group are more similar to each other than those in other groups.

In another example, computer vision methods (e.g., object recognition or facial recognition) may be used to computationally process an image against an individual presence profile. For example, the sensor analysis engine 205, 305, and/or 405 may include an image analysis engine that may computationally process feature vectors from a captured image and determine whether the feature vectors from the captured image have substantial correspondence with any individual presence profile. In an example, the individual presence profile may be stored locally on the storage system 214 of the drone 105 and/or the storage system 314 of the drone docking station 110 and provided in the local user repository 216 and/or 316, and/or stored remotely and managed at the service platform 130 to provide the remote service repository 416.

In another example, data from a device on an individual may be used to determine whether the individual is verified as a user of the drone. For example, short-range communication signals (e.g., near field communication, Bluetooth, etc.) received or detected by a drone 105/200 may be processed and/or analyzed to determine whether the signal was communicated by a device associated with a verified user. That is, the user profile 217 may store device identifiers (serial numbers, MAC addresses, IP addresses, etc.) for devices of the verified user, and may determine whether a packet or other communication received from a device contains a device identifier associated with a verified user.

In an embodiment, presence profiles stored in the respective user repositories 216, 316, and/or 416 are provided when an individual or group of individuals signs up for a drone service. Presence profiles may be continually updated based on updated observation data collected by the sensors 113-118 or data received from other sources (e.g., medical records, device identifiers received over a communications network, etc.). Thus, presence profiles may be used to accurately identify an individual based on current or recent sensor data.

In an example, if the sensor signal lacks substantial correspondence with the individual presence profiles of the local user repository 216 and/or 316, the drone 105 or the drone docking station 110 may provide the sensor signal, feature vectors of the sensor signal, and/or a compressed and/or encoded version of the sensor signal to the service platform 130/400 through the communication network 125. The sensor analysis engine 405 of the service platform 400 may computationally process the sensor signal (e.g., feature vectors of the sensor signal, the compressed and/or encoded sensor signal, and/or other variations of the sensor signal) by determining whether the sensor signal substantially corresponds with an individual presence profile stored remotely at the user repository 416 in the storage system 410. In a specific example, the local user repositories 216 and 316 at the storage systems 214 and 314 may store a first portion of the individual presence profile and the remote user repository 418 at the storage system 410 may store a second portion of the presence indication profiles.

If the sensor signals indicate that the monitored space 102 does not include a verified user of the drone, then the method 600 returns to block 602. If the sensor signals indicate that a verified individual is present, then the method 600 proceeds to block 606 where it is determined whether the individual who has been verified as a user of the drone requires medical assistance. For example, the sensor analysis engine 205, 305, and or 405 may determine, based on the sensor signals used to determine whether a verified individual is present in the monitored space 102 and/or sensor signals received after determining that the verified individual is present in the monitored space 102, whether those sensor signals satisfy any conditions that are stored in a condition profile that may be included in the service profiles 219, 319, and/or 419 of the storage systems 214, 314, and 410 respectively. In one embodiment, if the verified user or subject is a vehicle, building, or other non-living object, block 606 may determine whether the verified subject requires remedial attention (e.g., a repair).

Figure 8:
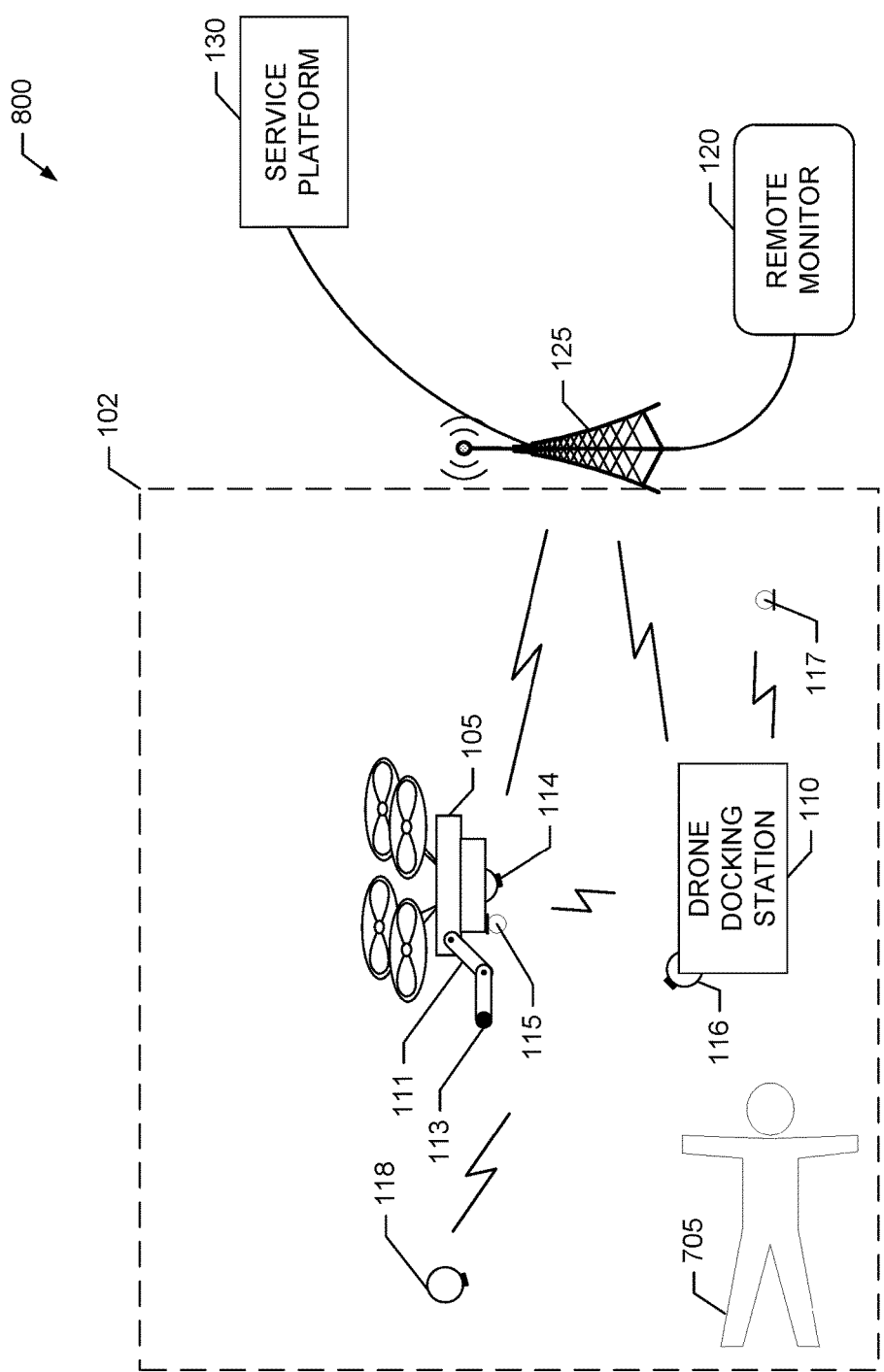
FIG. 8 is a further schematic view illustrating an embodiment of the drone data storage system during the method of FIG. 6.

In one example, the sensor analysis engines 205, 305, and/or 405 may be monitoring for various cues or actions provided by the individual via the acoustic sensors 115 and/or 117 and/or the imaging sensors 114, 116, and/or 118. As illustrated in FIG. 8, at least one of the imaging sensors 114, 116, and/or 118 may capture an image or series of images that, when computationally processed by the sensor analysis engine 205, 305, and/or 405, indicate the individual 705 is lying on the ground and/or moved to the ground within a predefined time period indicating that individual 705 collapsed. The condition of the individual lying on the ground and/or moved to the ground within a predefined time period may substantially correspond with a condition profile stored in the service repository 218, 318, and 418. In other examples, the individual may provide an audio cue and/or a visual cue that the sensor analysis engine 205, 305, and/or 405 recognizes as a condition to initiate an interaction with the individual. For example, the individual 705 may wave their hands at one or more of the imaging sensors 114, 116, and/or 118 and/or the individual 705 may speak a keyword and the acoustic energy received by an acoustic sensor 115 and/or 117 may be converted to an acoustic signal that the sensor analysis engine 205, 305, and/or 405 computationally processes against an acoustic profiles stored in the service profiles 219, 319, and 419 included in the service repository 218, 318, and 418. In another example, a lack of sensor data from an acoustic or imaging sensor may be indicative that a verified individual requires medical assistance. For example, if an ocular sensor cannot read a verified individual's eyes, such a lack of sensor data may be indicative of the individual being unconscious and in need of medical attention. Similarly, the drone 105/200 may be equipped with an acoustic emitter which can query an individual to determine whether a verified user requires medical assistance. The drone 105 may provide an interaction with the individual 705 and receive sensor data based on that interaction. For example, the drone 105 may provide through the acoustic emitter 224 an audible question. The individual 705 may provide a verbal response to the question to the drone 105, which the acoustic sensor 115 may provide as an audio signal to the sensor analysis engine 205 that may computationally process the audio signal against service profiles 219, 319, and/or 419 included in the service repository 218, 318, and/or 418, respectively. Upon substantial correspondence between the audio signal and the service profiles 219, 319, and/or 419 in the service repositories 218, 318, 418 that indicates no service is required, or lack of substantial correspondence with any of the service profiles 219, 319, and/or 419, the drone 105 may determine that the individual 805 does not require medical assistance, in which case the method 600 returns to block 602.

In an example, received sensor data may be processed to determine whether it is within an accepted range for such sensor data, and responsive to determining that the sensor data is outside of the accepted range, the drone 105/200 may determine that medical assistance is necessary. For example, the drone 105/200 may include one or more biometric sensors, such as temperature sensors for detecting a body temperature of an individual (e.g., a temporal scanner capable of reading a temperature of an individual's forehead); if the detected body temperature is outside of an accepted range for the data, the individual may require medical assistance. In yet another example, the condition may be based on the environment of the monitored space 102 such as time of day, an event occurring in the monitored space (e.g., a concert, a race, etc.), weather conditions, and/or the location of the monitored space.

In one embodiment, the condition may be based on a cues or actions by an individual other than the individual verified as a user of the drone. For example, a third party may yell for help, and acoustic energy received by an acoustic sensor 115 and/or 117 may be converted to an acoustic signal that the sensor analysis engine 205, 305, and/or 405 computationally processes against an acoustic profiles stored in the service profiles 219, 319, and 419 included in the service repository 218, 318, and 418.

In a further example, the drone 105/200 may receive from a device of the individual 705 an indication that the individual 705 requires medical assistance. For example, an indication of an elevated heart rate detected by a smart watch or fitness band used by the individual 705 may be received by the drone 105/200. The drone 105/200 may utilize one or more sensors 113-118 to confirm a determination that the user requires medical assistance. For example, in some instances, an elevated heart rate may be caused by the individual 705 exercising; upon analysis of image data obtained by an imaging sensor 114, the drone 105/200 may determine that the individual 705 does not require medical assistance. Correspondingly, if the elevated heart rate is not caused by the individual 705 exercising, and an acoustic sensor 115 or 117 determines that the individual is breathing laboriously, the drone 105/200 may determine that the individual 705 requires medical assistance.

In another example, the drone 105/200 may receive a communication from another device (e.g., an emergency alert system, a weather station, etc.) that indicates that an individual or group of individuals is likely to require medical assistance. For example, a drone 105/200, drone docking station, remote monitor, or service platform may receive and monitor information from any number of sources, such as television or radio broadcasts, or network-based sources of data (e.g., Internet websites, etc.). Analysis of such data may indicate that a mass casualty event is occurring, such as a weather-related emergency, a large traffic accident, or a sudden outbreak of a widespread illness. The drone 105/200 may, in response, navigate itself to a location proximate to the mass casualty event, and determine, based on sensor data, whether any of the individuals potentially affected by the event are verified users of the drone, and in turn, determine whether the users require medical assistance. Additionally, in one example, the drone may also determine whether unverified users of the drone require medical assistance, and communicate with emergency medical personnel to alert those personnel of details of the required medical assistance. For example, analysis of data from imaging sensors or acoustic sensors may identify a need for defibrillators or other specific medical equipment.

In one embodiment, the particular sensor signals used at block 606 to determine whether the individual who has been verified as a user of the drone require medical assistance are determined based on the sensor signals used to verify the user. For example, if an imaging sensor was used to verify the individual as a user of the drone, an acoustic sensor may be utilized to determine whether the verified user requires medical assistance. Likewise, if a combination of imaging sensor data was used to verify the user, and a lack of acoustic sensor data is identified when querying the user, the drone 105/200 may determine that biometric sensor data should be obtained to determine whether the individual requires medical assistance.

If a verified individual does not require medical assistance, then the method 600 may return to block 602 where the drone data storage system 100 may continue to monitor the monitored space 102 to collect data as described with respect to block 602, and may continue to determine whether a condition exists in the monitored space 102 at block 606 with respect to a verified individual.

If a verified individual is determined to require medical assistance, then the method 600 may continue to block 608, where the drone 105 accesses health data associated with the user corresponding to the verified individual. In one embodiment, the drone 105 accesses health data stored on the drone itself, e.g., as part of a user profile 217. In one embodiment, the drone 105 may access health data stored by another drone, a drone docking station 300, a service platform 400, or by a third party repository of health data. In one embodiment, if the observed, verified subject is a vehicle, building, or other non-living object, the drone 105 may access observation data associated with the object. In one embodiment, at block 608, the drone 105 may also send a communication to additional users (e.g., family members or community members) to notify those users that the verified individual requires medical assistance.

In one embodiment, the determination by drone 105 may trigger a call for assistance, for example, to an ambulance or health care facility to request medical personnel. In one embodiment, in response to the determination that the verified individual requires medical assistance, drone 105 may detect the presence of other individuals (whether users of the drone or not), access the health data of the verified individual, and use acoustic emitter 224 to convey instructions to the other individuals to treat a medical condition of the user. For example, because the drone 105 stores or has access to the health data of the individual 805, the drone 105 may identify a likely condition of the individual. As one example, the individual 805 may have a food allergy to a common ingredient, and the drone 105 may utilize GPS coordinates obtained by positioning system 228 to determine that the drone 105 (and the individual 805) is proximate to a restaurant. Responsive to such information, the drone 105 may instruct another individual that the verified individual carries an epinephrine injector, and instruct the individual to administer the epinephrine to the verified individual in need of assistance. Other contextual data may also be utilized to determine the particular type of medical assistance needed, which can be conveyed to medical personnel or other nearby users.

Method 600 then continues to block 610. At block 610, the health data associated with the user may be transmitted to a third party, or observation data associated with a subject may be transmitted to a third party. For example, the health data associated with the user may be transmitted to medical personnel attending to the user in need of assistance. In one embodiment, only pertinent information is transmitted to the medical personnel; for example, information related to a heart condition may be transmitted to the medical personnel, but other data may remain private without explicit consent to divulge such data to the medical personnel from the user or from an authorized user (e.g., a family member or guardian). In one embodiment, the health data may be transmitted to another drone associated with a third party. Method 600 may then return to block 602 and monitor and collect observation data. In one embodiment, the information related to the need for medical assistance is stored in the observation data.

In an embodiment, the sensor analysis engine 205, 305, and/or 405 may determine an apparent position of the individual such as a relative direction from which acoustic energy is being provided by the individual and/or the approximate location of the individual. For example, the drone data storage system 100 may include the acoustic sensors 115 and 117 that are positioned about monitored space 102 to receive acoustic energy and capture audio signals within the monitored space 102. The sensor analysis engines 205 and/or 305 may create a time stamp that includes the time at which each acoustic sensor 115 and 117 captured the audio signal. The sensor analysis engines 205 and/or 305 may then use known positions of the acoustic sensors 115 and 117 along with the time stamps that indicate when each acoustic sensor 115 and 117 captured the audio signal to determine the source location of the audio signal based on time-difference-of-arrival (TDOA) and triangulation techniques. In another example, the acoustic sensors 115 and 117 may be directionally-discriminating acoustic sensors that are configured to determine the general direction from which acoustic energy is being provided. The sensor analysis engine 205 and 305 may then provide the apparent position to the mobility controller 207 of the drone 105/200 such that the drone 105/200 may autonomously navigate toward the apparent position of the individual 705 providing the acoustic energy.

In another example, the imaging sensor 114, 116, and/or 118 of the drone data storage system 100 may be used to determine the apparent position of the individual 705. In an example, the imaging sensor 114 may be positioned at an angle while directed at the individual 705 and while the drone 105 is hovering above the ground. When an image is captured of the individual 705 by the imaging sensor 114, other sensor data may be gathered as well, which may include position data from the positioning system 228 of the drone 105 when the image was captured, the angle of the imaging sensor 114 when the image was captured, and the distance the drone 105 is from the ground, which may be provided by an altimeter included on the drone 105. Based on the angle of the imaging sensor 114 and the distance between the ground and the drone 105, the sensor analysis engine 205 may determine the horizontal distance between the drone 105 and the individual 705. Based on the horizontal distance and the positioning coordinates of the drone 105, the sensor analysis engine 205 may determine the positioning coordinates of the individual 705, which are then provided to the mobility controller 207 of the drone 105 such that the drone 105/200 may autonomously navigate toward those positioning coordinates of the individual 705.

The drone 105/200 and/or the drone docking station 110/300 may be continually monitoring the monitored space 102 while the drone 105/200 is in-flight toward the apparent source of the individual 705. The drone 105 may autonomously navigate toward the position of the individual 705 until the drone is within a predetermined range of that position. For example, the drone 105 may be within 1 foot, 2 feet, 5 feet, 10 feet, 20 feet, or any other predetermined range. The predetermined range may be based on the condition that caused the drone to be in the in-flight mode. For example, when the individual is on the ground, the predetermined range may be 2 feet, while if the individual 705 was waving to the drone 105, the predetermined range may be 10 feet. When the drone 105 arrives within the predetermined range of the individual, the drone 105 may enter an investigate mode where the drone 105 hovers within the predetermined range of the individual 705.

The drone controller 204, the drone docking engine 304, and/or the services engine 404 may include machine learning/artificial intelligence algorithms to learn what conditions may require further investigation to determine whether a user requires a service such as medical assistance and what conditions do not require investigation to determine whether an individual requires a service. If conditions are present where the drone data storage system 100 identifies that a service is required but upon further investigation and/or interaction with the individual determines that no service is required, the drone controller 204, the drone docking engine 304, and/or the services engine 404 may update the condition profiles, the individual presence profiles, and/or other information in the user profiles 217, 317, and/or 417 and service profiles 219, 319, and/or 419 to indicate that service was not needed based on the conditions that caused the drone 105 to be "in-flight" and to investigate the condition. The drone controller 204, the drone docking engine 304, and/or the services engine 404 may be configured with one or more machine learning algorithms to perform supervised machine learning, unsupervised machine learning (e.g., deep belief networks, neural networks, statistical pattern recognition, rule-based artificial intelligence, etc.) semi-supervised learning, reinforcement learning, deep learning, and other machine learning algorithms when updating, creating, and/or reinforcing a condition profile, an individual presence profile, a service profile, 219, 319, and/or 419, a user profile 217, 317, and/or 417, and/or any other profile stored in the user repositories 215, 316, and/or 416 and service repositories 218, 318, and/or 418 discussed herein that is updatable over time based on received sensor signals.

Figure 9:
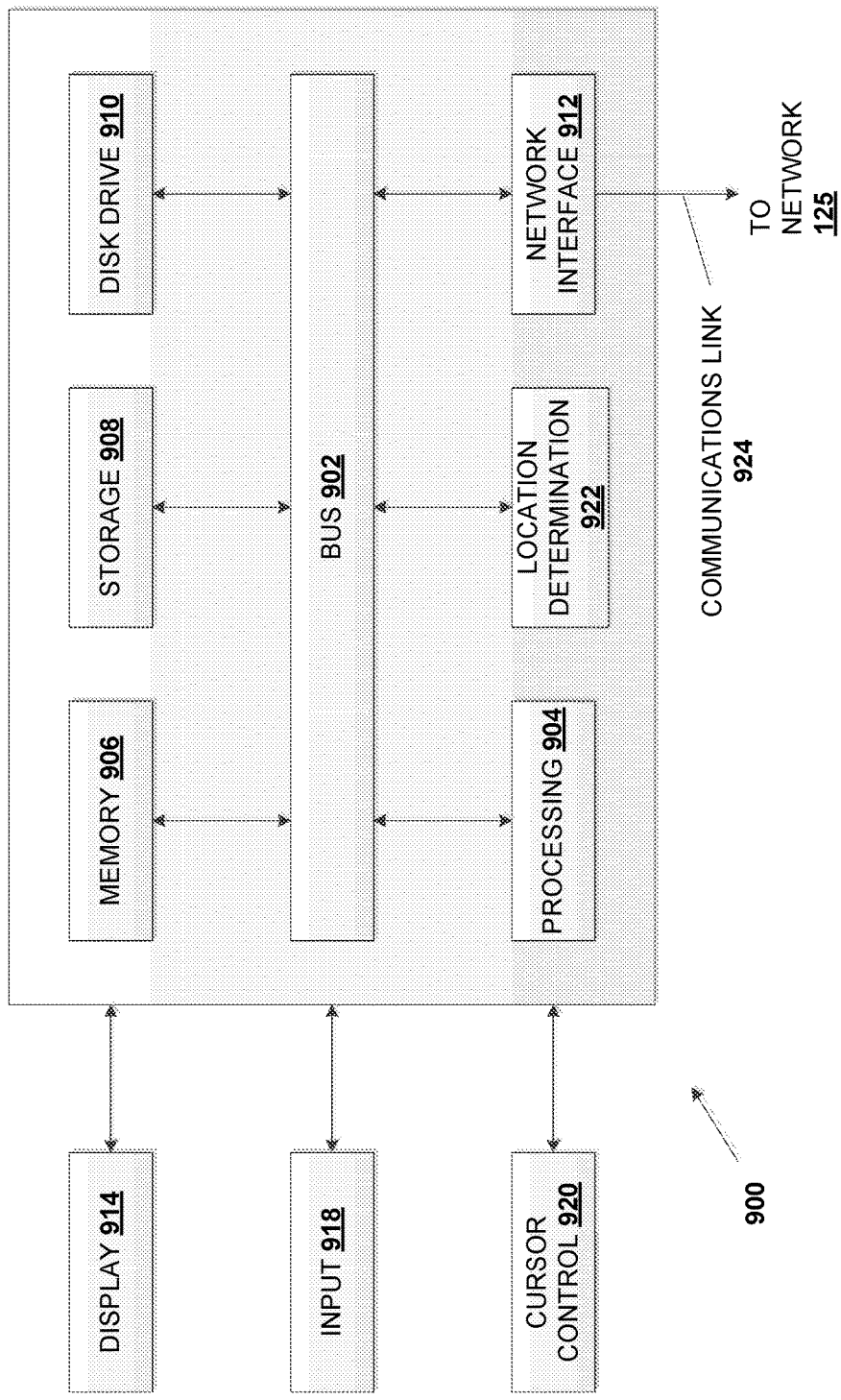
FIG. 9 is a schematic view illustrating an embodiment of a computer system.

Referring now to FIG. 9, an embodiment of a computer system 900 suitable for implementing, for example, the control of the drones 105 and/or 200, the drone docking stations 110 and/or 300, the remote monitor 120 and/or 500 and the service platforms 130 and/or 400, is illustrated. It should be appreciated that other devices utilized in the drone storage system 100/700 discussed above may be implemented as the computer system 900 in a manner as follows.

In accordance with various embodiments of the present disclosure, computer system 900, such as a computer and/or a network server, includes a bus 902 or other communication mechanism for communicating information, which interconnects subsystems and components, such as a processing component 904 (e.g., processor, micro-controller, digital signal processor (DSP), etc.), a system memory component 906 (e.g., RAM), a static storage component 908 (e.g., ROM), a disk drive component 910 (e.g., magnetic or optical), a network interface component 912 (e.g., modem or Ethernet card), a display component 914 (e.g., CRT or LCD), an input component 918 (e.g., keyboard, keypad, or virtual keyboard), a cursor control component 920 (e.g., mouse, pointer, or trackball), and/or a location determination component 922 (e.g., a Global Positioning System (GPS) device as illustrated, a cell tower triangulation device, and/or a variety of other location determination devices.) In one implementation, the disk drive component 910 may comprise a database having one or more disk drive components.

In accordance with embodiments of the present disclosure, the computer system 900 performs specific operations by the processing component 904 executing one or more sequences of instructions contained in the system memory component 906, such as described herein with respect to the drone(s), the drone docking station(s), the service platform, and/or the remote monitor(s). Such instructions may be read into the system memory component 906 from another computer-readable medium, such as the static storage component 908 or the disk drive component 910. In other embodiments, hardwired circuitry may be used in place of or in combination with software instructions to implement the present disclosure.

Logic may be encoded in a computer-readable medium, which may refer to any medium that participates in providing instructions to the processing component 904 for execution. Such a medium may take many forms, including but not limited to, non-volatile media, volatile media, and tangible media employed incident to a transmission. In various embodiments, the computer-readable medium is non-transitory. In various implementations, non-volatile media includes optical or magnetic disks and flash memory, such as the disk drive component 910, volatile media includes dynamic memory, such as the system memory component 906, and tangible media employed incident to a transmission includes coaxial cables, copper wire, and fiber optics, including wires that comprise the bus 902 together with buffer and driver circuits incident thereto.

Some common forms of computer-readable media include, for example, floppy disk, flexible disk, hard disk, magnetic tape, any other magnetic medium, CD-ROM, DVD-ROM, any other optical medium, any other physical medium with patterns of holes, RAM, PROM, EPROM, FLASH-EPROM, any other memory chip or cartridge, cloud storage, or any other medium from which a computer is adapted to read. In various embodiments, the computer-readable media are non-transitory.

In various embodiments of the present disclosure, execution of instruction sequences to practice the present disclosure may be performed by the computer system 900. In various other embodiments of the present disclosure, a plurality of the computer systems 900 coupled by a communication link 924 to a communication network 125 (e.g., such as a LAN, WLAN, PTSN, and/or various other wired or wireless networks, including telecommunications, mobile, and cellular phone networks) may perform instruction sequences to practice the present disclosure in coordination with one another.

The computer system 900 may transmit and receive messages, data, information and instructions, including one or more programs (e.g., application code) through the communication link 924 and the network interface component 912. The network interface component 912 may include an antenna, either separate or integrated, to enable transmission and reception via the communication link 924. Received program code may be executed by processor 904 as received and/or stored in disk drive component 910 or some other non-volatile storage component for execution.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the scope of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components, and vice versa.

Software, in accordance with the present disclosure, such as program code or data, may be stored on one or more computer-readable media. It is also contemplated that software identified herein may be implemented using one or more general-purpose or special-purpose computers and/or computer systems, networked and/or otherwise. Where applicable, the ordering of various steps described herein may be changed, combined into composite steps, and/or separated into sub-steps to provide features described herein.

The foregoing is not intended to limit the present disclosure to the precise forms or particular fields of use disclosed. As such, it is contemplated that various alternate embodiments and/or modifications to the present disclosure, whether explicitly described or implied herein, are possible. Persons of ordinary skill in the art in possession of the present disclosure will recognize that changes may be made in form and detail without departing from the scope of what is claimed.

What is claimed is:

1. An unmanned aerial vehicle apparatus comprising:
   a plurality of sensors, wherein the plurality of sensors includes at least an imaging sensor;
   at least one communications interface;
   at least one non-transitory memory storing identity data associated with one or more users and health data associated with the one or more users; and
   one or more processors coupled to the plurality of sensors, communications interface, and non-transitory memory and configured to execute instructions to cause the apparatus to:
   navigate the unmanned aerial vehicle to an area including one or more individuals;
   obtain, from a first subset of the plurality of sensors including at least the imaging sensor, sensor data corresponding to the one or more individuals;
   determine, based on the obtained sensor data and the stored identity data, that one of the one or more individuals corresponds to identity data of a user stored in the non-transitory memory;
   determine, using a second subset of the plurality of sensors, that the user corresponding to the identity data requires medical assistance, wherein the instructions to determine that the user corresponding to the identity data requires medical assistance further include instructions to cause the apparatus to process data received by the communications interface to determine that the user corresponding to the identity data requires medical assistance; and
   transmit, to a third party, health data associated with the user corresponding to the identity data.

2. The unmanned aerial vehicle of claim 1, wherein the first subset of the plurality of sensors further includes an acoustic sensor.

3. The unmanned aerial vehicle of claim 1, wherein the second subset of the plurality of sensors includes a biometric sensor.

4. The unmanned aerial vehicle of claim 1, wherein the unmanned aerial vehicle further comprises an acoustic emitter, and wherein the instructions further cause the apparatus to audibly emit, using the acoustic emitter, care instructions associated with the user corresponding to the identity data.

5. The unmanned aerial vehicle of claim 1, wherein the user is a first user, and wherein the instructions to cause the apparatus to determine, using a second subset of the plurality of sensors, that the first user corresponding to the identity data requires medical assistance further cause the apparatus to process sensor data, captured by an acoustic sensor from a second user, to determine that the first user corresponding to the identity data requires medical assistance.

6. The unmanned aerial vehicle of claim 1, wherein the instructions further cause the apparatus to determine, based on the imaging sensor data, one or more sensors to be included in the second subset of the plurality of sensors.

7. A method of transmitting data, the method comprising:
   navigating an unmanned aerial vehicle to an area including one or more individuals;
   obtaining, from a first subset of a plurality of sensors on the unmanned aerial vehicle, including at least an imaging sensor, sensor data corresponding to the one or more individuals;
   determining, based on the obtained sensor data and stored identity data, that one of the one or more individuals corresponds to identity data of a user stored on the unmanned aerial vehicle;
   determining, based at least on imaging sensor data from the imaging sensor, one or more sensors to be included in a second subset of the plurality of sensors on the unmanned aerial vehicle;
   determining, using the second subset of the plurality of sensors on the unmanned aerial vehicle, that the user corresponding to the identity data requires medical assistance; and
   transmitting, to a third party, stored health data associated with the user corresponding to the identity data.

8. The method of claim 7, wherein the first subset of the plurality of sensors further includes an acoustic sensor.

9. The method of claim 7, wherein the second subset of the plurality of sensors includes a biometric sensor.

10. The method of claim 7, further comprising audibly emitting, using an acoustic emitter on the unmanned aerial vehicle, care instructions associated with the user corresponding to the identity data.

11. The method of claim 7, wherein the user is a first user, and wherein determining, using the second subset of the plurality of sensors, that the first user corresponding to the identity data requires medical assistance further includes processing sensor data, captured by an acoustic sensor from a second user, to determine that the first user corresponding to the identity data requires medical assistance.

12. The method of claim 7, wherein determining, using a second subset of the plurality of sensors, that the user corresponding to the identity data requires medical assistance further includes processing data received by the communications interface to determine that the first user corresponding to the identity data requires medical assistance.

13. A non-transitory machine-readable medium having stored thereon machine-readable instructions executable to cause a machine to perform operations comprising:
   navigating an unmanned aerial vehicle to an area including one or more individuals;
   obtaining, from a first subset of a plurality of sensors on the unmanned aerial vehicle, including at least an imaging sensor and an acoustic sensor, sensor data corresponding to the one or more individuals;
   determining, based on the obtained sensor data and stored identity data, that one of the one or more individuals corresponds to identity data of a user stored on the unmanned aerial vehicle;
   determining, using a second subset of the plurality of sensors on the unmanned aerial vehicle including at least a biometric sensor, that the user corresponding to the identity data requires medical assistance; and
   transmitting, to a third party, stored health data associated with the user corresponding to the identity data.

14. The non-transitory machine-readable medium of claim 13, the operations further comprising audibly emitting, using an acoustic emitter on the unmanned aerial vehicle, care instructions associated with the user corresponding to the identity data.

15. The non-transitory machine-readable medium of claim 13, wherein the user is a first user, and wherein determining, using the second subset of the plurality of sensors, that the first user corresponding to the identity data requires medical assistance further includes processing sensor data, captured by an acoustic sensor from a second user, to determine that the first user corresponding to the identity data requires medical assistance.

16. The non-transitory machine-readable medium of claim 13, wherein determining, using a second subset of the plurality of sensors, that the user corresponding to the identity data requires medical assistance further includes processing data received by the communications interface to determine that the first user corresponding to the identity data requires medical assistance.

17. The non-transitory machine-readable medium of claim 13, the operations further comprising determining, based on the imaging sensor data, one or more sensors to be included in the second subset of the plurality of sensors.

* * * * *